| United States Patent [19] | [11] | 4,136,094 |
|---|---|---|
| Condie | [45] | Jan. 23, 1979 |

[54] PREPARATION OF INTRAVENOUS HUMAN AND ANIMAL GAMMA GLOBULINS AND ISOLATION OF ALBUMIN

[75] Inventor: Richard M. Condie, Minneapolis, Minn.

[73] Assignee: The Regents of the University of Minnesota, Minneapolis, Minn.

[21] Appl. No.: 829,565

[22] Filed: Aug. 31, 1977

[51] Int. Cl.$^2$ .................... A23J 1/06; A61K 37/04
[52] U.S. Cl. .................... 260/122; 260/112 B; 424/101; 424/177
[58] Field of Search .................... 260/112 B, 122; 424/101, 177

[56] References Cited

U.S. PATENT DOCUMENTS

| 3,686,395 | 8/1972 | Stephan .................... 424/101 |
|---|---|---|
| 3,763,135 | 10/1973 | Shanbrom et al. .................... 260/112 B |
| 3,869,436 | 3/1976 | Falksveden .................... 260/112 B |
| 3,903,262 | 9/1975 | Pappenhagen et al. .................... 260/112 B X |
| 3,916,026 | 10/1975 | Stephan .................... 424/177 |
| 3,966,906 | 6/1976 | Schultze et al. .................... 260/112 B X |
| 3,998,946 | 12/1976 | Condie et al. .................... 424/101 |
| 4,025,500 | 5/1977 | Garcia et al. .................... 260/112 B |

*Primary Examiner*—Walter C. Danison
*Attorney, Agent, or Firm*—Burd, Braddock & Bartz

[57] ABSTRACT

A method of isolating and purifying natural, unaltered, undenatured immune gamma globulin (IgG) for intravenous administration and albumin from animal blood plasma, especially human, and the resulting products. The method involves the initial stabilization of plasma by treatment with silica, or the use of previously stabilized plasma. IgG and albumin are isolated from the stabilized plasma by chromatographic reaction with sterile ion exchange resin and eluted by adjustment of pH and ionic strength. The products are concentrated, purified further and packaged. They are characterized by high yield and high purity. They are unfragmented and unaggregated, i.e., natural preparation.

15 Claims, 1 Drawing Figure

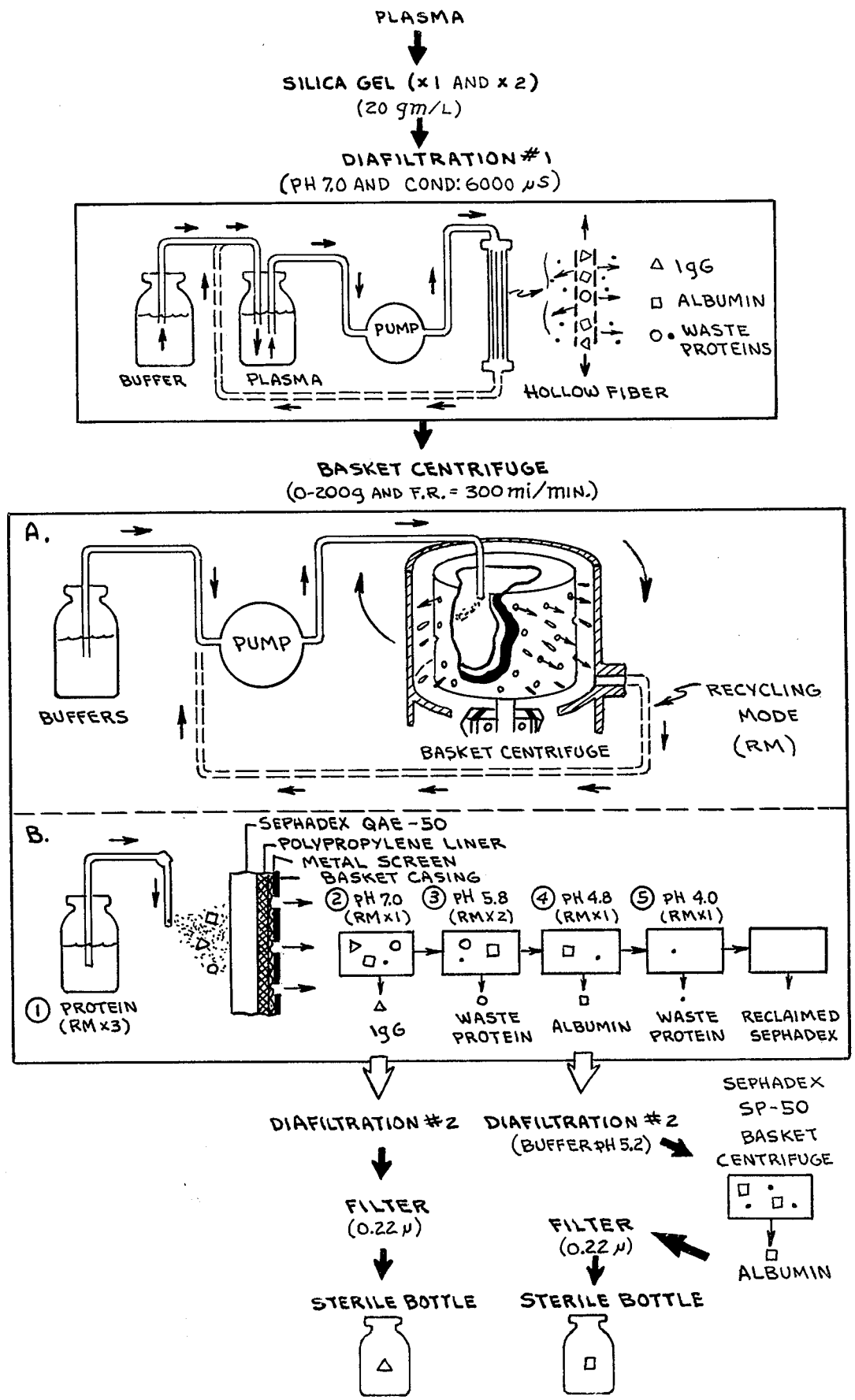

PREPARATION OF INTRAVENOUS HUMAN AND ANIMAL GAMMA GLOBULINS AND ISOLATION OF ALBUMIN

The invention described herein was made in part in the course of work under a grant or award from the Department of Health, Education and Welfare.

BACKGROUND OF THE INVENTION

1. Field of the Invention

The invention relates to a process for the fractionation of animal blood plasma and the isolation and purification of natural, unaltered, undenatured immune gamma globulin and albumin. More particularly, the invention relates to the preparation of intravenously injectable human immune gamma globulin.

The plasma fractionation industry in this country and Europe currently uses the method of cold ethanol fractionation developed by Dr. E. J. Cohn of Harvard University in the 1940's. Even though new methods of protein separation have evolved in the ensuing 35 years, the industry has neither chosen to gamble on new methods nor face up to any regulatory inhibition that a new product faces. As a result of this lack of new spirit, no methods have been developed to produce a new large scale system that would lead to a cheaper and better product. It has been demonstrated that there are severe limitations to the Cohn method, the major being that the process does indeed denature some of the proteins which it attempts to purify and isolate.

Several years have been spent in the development of methods and technology for the preparation and purification of animal (horse, goat and rabbit plasma with antibodies against human lymphocytes) plasma. This anti-lymphocyte globulin, a biologic immunosuppressive agent termed ALG, has been demonstrated to have potent immunosuppressive activity against cell mediated immunity, the type of immunity that causes grafts to be rejected.

After demonstrating the efficacy of this material in animals, it was sought to bring this to the clinic as an adjunctive immunosuppressive agent in the management of the human renal transplant patients. At the time of clinical application of this material, it was felt that the following criteria had to be established: safety of the preparation, a method for fractionating and isolating maximal activity in plasma and a method of fractionation that would allow administration of this material to patients by the most effective route. Animal experiments had demonstrated that the administration of the same quantity of IgG by the intravenous route was two to three fold more effective than the intramuscular or other route. In addition, only limited quantities can be administered intramuscularly whereas 10 to 100 times as much can be administered intravenously. Therefore it was sought to produce a preparation of horse anti-lymphocyte globulin that could be administered safely by the intravenous route. This was done with full knowledge that human gamma globulin could not be administered by the intravenous route.

Early studies by Good at Minnesota, Janeway at Harvard, and others, had demonstrated that the intravenous administration of the Cohn fractionated human gamma globulin often produced severe systemic reactions. The cause of these reactions was related to the high concentration of aggregated material due to the presence of a protein denaturing agent found in the fraction removed by the present invention. As a result, the only approved method for fractionation is the Cohn cold ethanol process and the only approved route of administration of gamma globulin today is the intramuscular route.

Since intravenous administration of fresh plasma produces no reaction, it has been accepted that the aggregated materials were there as a result of the denaturation of the gamma globulin by the alcohol method and, therefore, alternative methods were sought for the purification and preparation of the horse globulin materials. That this has been successful, and that the goal has been achieved of preparing a safe globulin that can be administered intravenously in patients, is supported by the following facts. Up to the present, over 30,000 grams of purified horse anti-lymphocyte globulin have been prepared. This material has been administered intravenously to over 900 renal transplant patients. The total experience with intravenous administrations approaches over 13,000 separate administrations. These intravenous administrations have not been associated with any evidence of reaction at the time of administration. It therefore was felt that the methods utilized in the preparation and isolation of these horse, goat and rabbit gamma globulins could resolve the problems associated with the attempts to produce and prepare from human plasma an intravenous gamma globulin for use in treating life threatening viral and bacterial infections.

Since viral and bacterial infections constitute the leading cause of patient death in renal transplantation, methods were sought that could be used to treat these severe life threatening infections. One attractive approach was the use of a human gamma globulin that could be administered intravenously. Knowing that none of the commercial preparations could be used in this manner, the possibility was explored of fractionating human gamma globulin from plasma according to the methods developed for the fractionation of the animal proteins. It was found in general principle that this could be done. In clinical studies with this new IV human gamma globulin, doses have been administered intravenously ranging from 20 mg/kg/day to 200 mg/kg/day over a 14 day period. Studies to date show promise of establishing efficacy of the intravenous administration of gamma globulin isolated from pooled human plasma in the treatment of life threatening viral and bacterial infections in immunologically compromised patients.

2. Description of the Prior Art

Although there have been numerous attempts to produce an intravenously injectable gamma globulin, none to our knowledge has produced a natural, unaltered and undenatured product. These efforts are reviewed in Stephan (Biotest) U.S. Pat. No. 3,916,026 and Pappenhagen et al (Cutter) U.S. Pat. No. 3,903,262. The Stephan patent discloses the preparation of intravenously injectable non-complement binding gamma globulin by treating complement binding gamma globulin with beta-propiolactone. The Pappenhagen et al patent discloses preparing intravenously injectable modified immune serum globulin by cleaving at least one interchain disulfide linkage of intact immune serum globulin chains having intact intrachain disulfide linkages and replacing the cleaved disulfide linkage with a pair of alkylate mercapto groups.

SUMMARY OF THE INVENTION

The methods and technologies of the present invention are characterized by 1) their extreme simplicity, 2) the speed and rapidity that each step can be performed, 3) the lack of rigid temperature control required since most of the steps can be carried out at room temperature, and 4) the fact that the method can be scaled up to infinitely large industrial scale volumes at a fraction of the current Cohn costs. In addition, the products are "native", natural, undenatured, aggregate-free, sterile, free from virus and can be isolated in higher yields than with the alcohol fractionation method and in a purer state.

The method involves three basic manipulations. The first step: plasma stabilization, the second: isolation and elution from ion exchange resins of gamma globulin and albumin, and the third step: concentration, dialysis and sterile filtration. The plasma stabilization step comprises treatment with fumed colloidal silica by admixing plasma with silica and then separating stabilized plasma from the silica with adsorbed constituents. The stabilization requires one hour to complete and accomplishes removal of a number of aggregable and easily denaturable plasma proteins. Also removed are the hepatitis associated antigen in plasma and a number of proteolytic enzymes and their precursors. The presence of these enzymes otherwise can lead to the degradation and aggregation of other plasma proteins and the activation of the kinin system. The stabilized plasma is then ready for the next step or can be filter-sterilized and stored at room temperature for periods exceeding two years. Storage of stabilized plasma at room temperature for periods exceeding two years does not alter its biological support properties and no increases in turbidity or precipitation have been observed.

The second step involves the isolation of the IgG and albumin from the stabilized plasma by reacting this material with a sterile ion exchange resin. The IgG and albumin are eluted by adjustments of pH and ionic strength. In addition, pyrogenic activity of plasma is removed by these resins. This ion exchange separation step requires approximately 40 minutes and results in the isolation of an undenatured, monomeric (molecular weight 160,000) aggregate free human IgG 99% pure, with yields of between 60-70%. The I.V. IgG contains less than 1% aggregates and less than 1% dissociated materials. The albumin can then be recovered with over 97% purity and with yields of between 80-90%, compared to the less than 50% yields of the Cohn method. The final step involves the concentration, dialysis, and sterile filtration of these plasma proteins. This final step requires between two to three hours for completion.

As illustrated by the examples, the process is readily scaled up for large capacity production. Although processing of lots of 4 liters and 100 liters are described in detail, lots of 1000 liters or more can readily be processed on existing equipment.

The final products have been subjected to the standard quality control tests that have been set forth by the Bureau of Biologics. These tests include testing for sterility, pyrogenic activity, and toxicity. In addition, tests for aggregation, deaggregation and molecular weight have been performed. Finally, these materials have been tested for and shown to be free of hepatitis associated antigen, by radio immunoassay. Intravenous administration of large quantities (over 30 grams) in over 50 patients has shown no evidence of passage of hepatitis virus nor produced cases of hepatitis.

BRIEF DESCRIPTION OF THE DRAWING

The invention is illustrated schematically, in flow sheet form, in the accompanying drawing.

DESCRIPTION OF THE PREFERRED EMBODIMENTS

Blood plasma or plasma fractions containing gamma globulin and/or albumin are stabilized by treatment with fumed silica (colloidal synthetic silicon dioxide of highest quality containing siloxan and silanol groups on its surface) according to the methods described in detail in Condie et al U.S. Pat. No. 3,998,946 or Stephan U.S. Pat. No. 3,686,395. The disclosures of these patents are incorporated herein by reference. Fresh or fresh frozen human or other animal blood plasma or outdated and/or cryoprecipitate human or other animal plasma may be used. The plasma product is intimately admixed with fumed silica, in either wet or dry form, followed by separation of the silica with its adsorbed lipoproteins, cholesterol, triglycerides, fibrinogen and plasminogen-plasmin enzyme system. The resulting stabilized purified plasma product may be stored or can immediately be treated to isolate the gamma globulin and albumin.

To increase yields, it is desirable to resuspend the separated silica, to recover trapped protein from the silica. The material is centrifuged and the supernatant is collected. The precipitate is desirably washed and the wash liquid and the recovered supernatant are added to the product from the silica treatment. The silica treated material is adjusted to the correct pH (about 7 ± 0.2), conductivity (about 6.0 ± 1.0 at 22° C) and volume by concentration and diafiltration or dialysis against an imidazole-acetate buffer (pH 7.0) in preparation for ion exchange treatment.

Although the gamma globulin and albumin may be isolated from the silica treated stabilized plasma product by column chromatography, it is preferred to use a basket centrifuge for its greatly increased flow rates. A variable speed centrifuge is used with speed settings for application of G forces from about 10 to about 250.

The ion exchange separation utilizes a strongly basic anion exchanger such as a sterile pre-swelled modified dextran with quaternary aminoethyl functional groups to separate the gamma globulin. An exemplary material is Sephadex QAE-50, composed of dextran chains cross-linked to give a three-dimensional polysaccharide network with quaternary aminoethyl groups attached by ether linkages to the glucose units of the dextran chains. The silica treated plasma is applied to the exchanger bed and recycled. pH 7.0 imidazole-acetate buffer is applied and pooled with IgG fraction.

Aliquots of pH 5.8 (± 0.1) imidazole-acetate buffer are applied, recycled and discarded. Then aliquots of pH 4.8 (± 0.1) imidazole-acetate buffer are applied to the QAE bed and recycled to separate the albumin fraction. After elution of the albumin from the initial ion exchanger, the albumin is purified by use of a further ion exchange material, a strongly acid cation exchanger such as a sterile modified dextran with sulphopropyl functional groups. An exemplary material, available as Sephadex SP-50, is composed of dextran chains cross-linked to give a three-dimensional polysaccharide network with sulphopropyl groups attached by ether linkages to the glucose units of the dextran chains.

The IgG and albumin pools are treated separately. The IgG is subjected to diafiltration against a glycine-saline buffer and, after sterile filtration, is bottled.

The albumin from the QAE chromatography is subjected to diafiltration against pH 5.2 (± 0.1) imidazole-acetate buffer and then to sulphopropyl chromatography. Although a column may be used, a basket centrifuge is preferred. The concentrated and purified albumin is subjected to final diafiltration against glycine-saline buffer and, after sterile filtration, is bottled.

EXAMPLE 1

The invention is further illustrated in the following detailed example of the preparation of human IgG and albumin:

1. Collection, Storage and Pooling of Human Plasma.

Both outdated and/or cryoprecipitate human plasma is obtained and is stored at $-20°$ C until it is to be used. Only hepatitis antigen tested plasma is used. The plasma is thawed at room temperature, and pooled, but not allowed to reach room temperature. Properties: Volume = 4.0L.; Conductivity = 11.4 millisiemens at 22° C (11.1–11.8); Protein Concentration = 59.2±2.8 mg/ml; pH = 7.50 (7.43–7.86); Time = 5–10 minutes (not including the time it takes to thaw the plasma).

| Volumes: (Starting 4.0 liters) | % of starting plasma |
|---|---|
| T.P. = 236.8 gm. ± 11.2 | 100 |
| Alb. = 157.6 gm. ± 18.8 | 100 |
| IgG = 37.2 gm. ± 4.4 | 100 |

2. Stabilization of Plasma: Removal of Fibrinogen, Plasminogen, Plasmin, Denatured Immunoglobulins and Lipoproteins Using $SiO_2$ Dry $SiO_2$ (Aerosil 380, Degussa, Inc., New York) is added to the plasma as it is stirred using a propeller stirrer until the final $SiO_2$ concentration is 20 g/L. Although stirring is continued for 1 hour at room temperature after the $SiO_2$ addition is completed, the reaction between $SiO_2$ and plasma is essentially completed in less than 20 minutes. The $SiO_2$ and bound components are removed by centrifugation at 6500 XG for 30 minutes at 0–4° C or by passing through a basket centrifuge or hollow fiber (300,000 or molecular weight pore size). The supernatant fluid is poured off and saved. The precipitate is washed with 0.9% NaCl solution to recover trapped protein. Albumin loss due to trappage in $SiO_2$ ppt. can be reduced as can IgG loss (See step No. 4). Properties: Volume = 3.4±0.4 L.; Conductivity = 11.8 millisiemens at 22° C (11.3–12.1); Protein Concentration = 54.0±2.2; pH = 7.40 (7.37–7.83); Time = 2 hours.

| | % of starting plasma |
|---|---|
| Volume = 3.4 L ± 0.4 | 85.5 |
| T.P. = 183.6 ± 7.5 | 77.5 |
| Alb. = 123.8 ± 8.5 | 78.6 |
| IgG = 26.2 | 78.2 |

3. Second $SiO_2$ Treatment

The supernatant fluid from step No. 2 is treated a second time with the same amount of $SiO_2$ (20 g/L. based on the original plasma volume) as in step No. 2. Aerosil and bound components are removed as before. Properties: Volume - 2.92 ± 0.3; Conductivity = 11.6 millisiemens at 22° C (11.2–12.3); Protein Concentration = 46.5 ± 2.6; pH = 7.35 (7.14–7.62); Time = 2 hours.

| | % of starting plasma |
|---|---|
| Volume = 2.92 ± 0.3 | 72.5 |
| T.P. = 135.8 ± 5.8 | 57.3 |
| Alb. = 119.0 ± 21.4 | 75.3 |
| IgG = 16.6 ± 3.5 | 44.6 |

4. Recovery of Plasma Proteins from $SiO_2$ Precipitates to Increase Yields.

To recover trapped protein from the $SiO_2$ precipitates from steps No. 2 and No. 3, the precipitates are resuspended with 500 ml. of 0.9% NaCl which is 12.5% of the original plasma volume and centrifuged at 6500 XG for 30 minutes at 0–4° C and the supernatant is collected. The precipitates are washed twice and the recovered supernatants are added to the material remaining after the second $SiO_2$ treatment. Then the process proceeds to diafiltration step No. 5.

| $SiO_2$ Washes: | | | | |
|---|---|---|---|---|
| | $SiO_2$ #1 Washes | | $SiO_2$ #2 Washes | |
| | Recovery | % Starting Plasma | Recovery | % Starting Plasma |
| Volume | 925 ml | 23 | 800 ml | 20 |
| T.P. | 21.3 g. | 9 | 27.5 g. | 12 |
| Alb. | 17.3 | 11 | 17.2 | 11 |
| IgG | 5.2 | 14 | 3.9 | 10 |
| $SiO_2$ Washes plus Post $SiO_2$ #2 | | | | |
| | | | | % starting plasma |
| Volume | 4.64 L. | | | 116 |
| T.P. | 184.6 g. | | | 78 |
| Alb. | 154 | | | 98 |
| IgG | 25.7 | | | 69 |

5. Diafiltration #1 Against pH 7.0 Imidazole-acetate buffer (#1)

The $SiO_2$ treated material is adjusted to the correct pH, conductivity and volume by concentration and diafiltration (or dialysis) in a Millipore Pellicon Membrane Concentrator (Millipore Corp., Bedford, Mass.) with 15 sq. feet of PTGC membrane (10,000 daltons cutoff) or another similar device using membranes with a molecular weight cutoff of 10,000 to 50,000 daltons. Diafiltration is accomplished by adding sterile pH 7.0 imidazole-acetate buffer (#1) at the same rate as filtrate is removed. Diafiltration is completed when the sample has reached pH 7.0 ± 0.05 at 22° C and conductivity is 6.0 ± 0.2 millisiemens at 22° C. Properties: Volume = 3.7 L.; Conductivity = 6.0 ± 0.2 at 22° C.; Protein Concentration = 50 mg/ml; g/g QAE = 0.94: pH = 7.0 ± 0.05; Time = 1 hour.

| | | | % starting plasma |
|---|---|---|---|
| Volume | = | 3.7 L. | 116 |
| T.P. | = | 184.6 g. | 78 |
| Alb. | = | 154 g. | 98 |
| IgG | = | 25.7 g. | 69 |

6. QAE-50 Chromatography (at 22° C).

A Western States STM-1000 basket centrifuge with a 12" × 5" basket lined with a 1 micron polypropylene liner is loaded with 197.2 g. Sephadex QAE-50 (preswelled in pH 7.0 imidazone-acetate buffer (#1). After the bed has been packed for ≈ minutes at 220 XG (1140 RPM), the speed of the centrifuge is reduced to 52 XG (550 RPM) and run another ≈5 minutes. The same buffer (#1) applied to bed through a Flood Jet ⅜ K1.5 nozzle at ≈0.3 L./minutes throughout packing procedure.

The sample (3.7 L. at 50.0 mg/ml, total protein — 185 gm) is now applied at 0.3 L./min and recycled twice. Then, 12.0 L. of the same pH 7.0 imidazole-acetate buffer (#1) are applied and pooled with the sample. This is the IgG fraction, (20 g at 1.6 mg/ml).

Then 4-4L. aliquots of pH 5.8 imidazole acetate buffer (#3) are applied — each aliquot is recycled once. This pool is discarded.

Next 4-4 L. aliquots of pH 4.8 imidazole-acetate buffer (#4) are applied — the first aliquot is recycled once. This 16 L. pool is the albumin fraction (126 g. at 7.9 mg/ml). If the gel is to be recycled for further use, 12 L. of pH 4.0 sodium acetate buffer (#2) is applied and discarded. Time = 4.5 - 5.0 hours. The basket centrifuge is run at 50 XG. Lower G forces appear to be desirable since larger quantities of protein/gm. of Sephadex can be applied without the breakthrough of contaminants.

|  | IgG Pool |  | Albumin Pool |  |
|---|---|---|---|---|
| Volume | 15.7 | L. | 16.0 | L. |
| Total protein | 19.7 | g. | 156.8 | g. |
| Protein conc. | 1.25 | g/L | 10.7 | g/L |
| pH | 7.0 |  | =4.9 |  |
| Conductivity | 6.2 | mS | 6.2 | mS |
| Flow rate | 0.3 | L/min. | 0.3 | L/min. |
| G/G QAE | 0.10 |  | 0.80 |  |
| % of starting plasma | 53.0 | (of IgG) | 88.6 | (of Alb.) |

The IgG and albumin pools are then treated separately: IgG to step #7; Albumin to step #9.

7. IgG Diafiltration #2 (at 4° C against glycine-saline buffer (#5) for IgG

| Final Values | Volume | Protein | pH | Cond. | Time | Flow Rate |
|---|---|---|---|---|---|---|
| IgG |  |  |  |  |  |  |
| Pool | 394 ml. | 50 mg/ml | 6.8±0.05 | 13 mS | 1 hr. | 350 ml/min |

8. (filter sterilely with 0.20 μ Pall Ultipor filter and dispense into 40 ml vials). Time = 1 hour.

Final IgG properties: pH 6.8; Conductivity 13 mS; Protein concentration 50 g/l; no measurable impurities. The product passed LAL, pyrogen and safety tests.

9. Albumin

Post QAE Albumin Pool:

| Albumin |  | 89.1 |
|---|---|---|
| $a_2$ macroglobulin - 3.7% |  | 2.5 |
| IgA - 2.3% |  | 1.6 |
| IgM - 1.7% |  | 1.3 |
| $a_1$ antitrypsin - 1.6% |  | 2.1 |
| Others - 3.6% |  | 3.4 |

10. Albumin Diafiltration #2 (at 4° C against pH 5.2 imidazole-acetate buffer (#6).

Final Values:

| Volume | = 3.14 L. |
|---|---|
| Protein | = 50 mg/ml |
| pH | = 5.20 ± 0.05 |
| Cond. | = 5500 mS |
| Time | = 1 hour |
| Flow rate | = 350 ml/min |

11. SP-50 Chromatography (at 22° C).

The sample is passed through Sephadex SP-50 (preswelled) in pH 5.2 imidazole-acetate buffer (#6). Basket centrifuge as described in step #6 or column may be used. Albumin Yield = 100% on this step.

12. Albumin Diafiltration #3 (at 4° C against glycine-saline buffer (#5).

Final Values:

| Volume | = 3.14 L. |
|---|---|
| Protein | = 50 mg/ml |
| pH | = 6.80 ± 0.05 |
| Conductivity | = 13 mS |
| Time | = 2.5 - 3 hours |
| Flow Rate | = 350 ml/min |

13. Bottle (filter sterilely with 0.20 μ Pall Ultipor filter and dispense into 40 ml vials). Time = 1 hour.

Final albumin properties: pH = 6.8; Conductivity = 13 mS; Prot. Conc. = 50 g/L; impurities 2.1%. The product passed LAL, pyrogen and safety tests.

The yields and recoveries are summarized in Table I:

TABLE I

|  | Plasma | SiO₂ #1 | SiO₂ #2 | SiO₂ & Washes | QAE | SP |
|---|---|---|---|---|---|---|
| Volume | 4.0 | 3.4±0.4 | 2.92±0.3 | 4.64 | — | — |
| % volume | 100 | 85.5 | 72.5 | 116 |  |  |
| Total protein | 2.36±11.2 | 183.6±7.5 | 135.8±5.8 | 184.6 | — | — |
| % T.P. | 100 | 77.5 | 57.3 | 78 |  |  |
| Albumin | 157.6±18.8 | 123.8±8.5 | 119.0±21.4 | 154.0 | 139.7 | 139. |
| % albumin | 100 | 78.6 | 75.3 | 98 | 88.6 | 88. |
| IgG | 37.2±4.4 | 26.2±3.7 | 16.6±3.5 | 25.7 | 19.7 | — |
| % IgG | 100 | 78.2 | 44.6 | 69 | 53.0 | — |
| Prot. Conc. | 59.2±2.8 | 54.0±2.2 | 46.5±2.0 | 29.8 | — | — |

The composition and properties of the buffers are set forth in Table II:

TABLE II 1. pH 7.0 Imidazole-acetate
   48.0 g. Imidazole
   610.0 g. sodium acetate
   80.1 ml 6.0M acetic acid
   15 gal. N.P. H₂O
   Cond = 6.15 ± 0.1 mS at 22° C
   pH = 7.0 ±0.05
2. pH 4.0 Sodium-acetate
   852.0 g. sodium-acetate
   1220.0 ml. glacial acetic acid
   15 gal. N.P. H₂O
   Cond = 6850 ± 0.1 mS

TABLE II-continued pH = 4.0 ± 0.05
3. pH 5.8 Imidazole acetate
   7.0 imidazole-acetate (#1)
   S    pH'ed with 4.0 sodium-acetate (#2)
        (≈4.5 L. pH 4) to 15 gal. of #1
4. pH 4.8 Imidazole-acetate
   7.0 imidazole-acetate (#1)
   pH'ed with 4.0 sodium-acetate (#2)
   (≈9.0 L. pH 4) to 15 gal. of #1
5. Glycine-saline
   1265 g. glycine
   498.8 g. NaCl
   15.0 gal. N.P. $H_2O$
   adjust pH with 5N NaOH to 6.80 ± 0.05
   (less 100 ml NaOH)
6. pH 5.2 Imidazole-Acetate Buffer-Full Capacity-5500 cond.
   S    22.33 g. imidazole
        169.4 g. NaAc
        51.0 ml. glacial HAc
        18 L. N.P. $H_2O$ (to bottom of cap)
        pH = 5.20 ± 0.05 Conductivity = 5500 μS±100 at 22° C

EXAMPLE 2

Large volume preparation of human intravenous gamma globulin is illustrated by the following:

1. Collection of human plasma from donors

Plasma is collected from healthy, volunteer adult donors. Aseptic techniques are utilized in the collection of this sterile plasma. It is either cryoprecipitated or outdated, is frozen at −20° to −70° C and stored sterilely in a closed storage environment. Individual records are kept on the cryoprecipitated plasma sources. It is not possible to always keep records on the pooled outdated plasma. However, only plasma that has been tested for hepatitis B associated antigen is used.

2. Preparation of pooled human plasma for protein fractionation

Preparation of the crude human plasma for fractionation of the gamma globulin is divided into the following steps: 1) prepooling safety testing, 2) pooling, (100 to 130 liter pools). Each lot of plasma is double checked to insure that it contains no hepatitis B-associated antigen. Then approximately 400–500 blood bags containing the human plasma are assembled, thawed, and pooled into a 220 liter sterile container. Samples are taken at this stage to test for hepatitis B-associated antigen, and then against appropriate viruses, bacteria and fungi, and against A and B human blood group substances. A total protein, gamma globulin concentration, albumin concentration, pH, and conductivity of the pool is determined.

One hundred liters are warmed at room temperature until thawed. However, the bags are immediately chilled at 4° C so they never reach room temperature. The bags are then immersed in 70% ethanol solution and the excess solution is drained off. Each bag is cut open and the contents poured fast into a sterile graduated cylinder, the volume recorded, and then poured into a sterile 220 liter polypropylene container. The pool is mixed and a sample removed for testing and sterility. The container of plasma is stored at 4° C overnight and then fractionated.

3. Fractionation of the crude pooled plasma

The pooled human plasma is fractionated according to the following outlined procedure:

A. Stabilization of the plasma by the addition of synthetic sterile pyrogen free silicon dioxide Dried, synthetic, sterile silicon dioxide (Aerosil 380) is added to a final concentration of 40 grams/liter of the pooled plasma. The plasma and silicon dioxide are mixed with the aid of motor driven rotors, care being taken to avoid foaming which can result in denaturation. This mixing is continued for one hour at room temperature. Following mixing, the silicon dioxide and its absorbed plasma proteins are placed in either a Beckman J6 centrifuge or a RC3 centrifuge for a thirty minute period and sedimented at 6,000 X G. Stabilization involved the removal of fibrinogen and any split products, the removal of the easily denaturable lipo-proteins and associated HLA antigens, and finally the removal of the plasminogen-plasmin, a proteolytic enzyme system which has been implicated in IgG aggregate formation and the partial degradation of gamma globulin. The supernate from the low speed centrifugation is pooled and run through a high speed continuous flow rotor at 32,800 X G to remove any other aggregated materials. This step is accomplished at +4° C at a rate of 350 ml/minute. The rotor is sterilized with 70% ethanol and rinsed with non-pyrogenic water prior to use. A post HSS sample is removed for biuret protein concentration determination.

B. Dialysis and concentration of the post silicon dioxide stabilized treated plasma pool Following the high speed spin, the protein concentration of the sample is adjusted to 50 g/l and diafiltrated with pH 7.0 imidazole acetate buffer (pH = 7.00 ± 0.05 and conductivity = 6.0 ± 0.1 mS at 22° C). One of two methods may be used:

i. Using an Amicon DC-30 unit with three cartridges with surface areas each 10 sq. ft. with a 50,000 MW cutoff, the pool is concentrated to about 50 g/l. Diafiltration is then accomplished by adding the imidazole-acetate buffer through a sterile 0.20 micron Pall Ultipor DFA 3001 ARP filter (a non-asbestos, non-glass fiber containing filter) to the pool as the concentration continues, so that the volume remains constant. The operation is concluded when the sample has a pH of 7.0 ± 0.05 and conductivity of 6.0 ± 0.1 mS. This is usually accomplished after 3–4 volumes of buffer have been added. The DC-30 is cleaned with a 0.1 N NaOH and 0.05% sodium hypochlorite, rinsed with a large volume of non-pyrogenic $H_2O$ and stored in 25% ethanol.

ii. This method is similar to method i but uses a Millipore Pellicon Apparatus equipped with 25 sq. ft of membrane with a 10,000 MW cut-off. The same procedure is followed and the Pellicon is cleaned with 0.1 NaOH, then 5% acetic acid, rinsed with non-pyrogenic $H_2O$ and stored in 25% ethyl alcohol.

In both methods i and ii samples of the pool and the filtrate are collected for biuret protein concentration determination.

C. Sterile filtration of the pool through 0.22 micron Millipore of Pall filters as an intermediate sterilization step in the procedure

D. Fractionation of human gamma globulin i. QAE Sephadex columns

Anion exchange chromatography is done using four 16 l bed capacity stacks containing about 650 g each Sephadex QAE A50 gel swelled in 2.87 mS pH 7.0 ±

0.05 imidazole-acetate buffer containing 25% ethanol. The stacks and all the tubing are sterilized by leaving them in this buffer for at least 24 hours. The buffer is washed out just prior to use with starting buffer filtered through a sterile 0.2 micron Pall filter. The stacks are arranged in parallel flow and the flow rate is kept constant at 150 ml/min/stack using gravity as the driving force. The sample, previously diafiltrated to meet specified conditions of pH 7.0 ± 0.05 and conductivity of 6.0 ± 0.1 mS at 22° C is spun at 6,500 X G for 30 min. at 22° C and then applied to the top of the stacks and samples are collected in sterile 4.0 l graduated cylinders. The column is monitored by following the absorbance at 280 nm of the protein peak. After ½ of the sample has been applied, the rest of the protein unbound to the gel is washed out using the sterile pH 7.0 imidazole-acetate buffer. The protein is pooled into a sterile polypropylene container and stored at 4° C until the second half of the sample can be added to it. The stacks are recycled by running at 2 bed volumes of pH 5.0 0.1 ionic strength acetate buffer, 2 bed volumes of pH 4.0 0.1 ionic strength acetate buffer, and 3 bed volumes of pH 7.0 0.1 ionic strength imidazole-acetate buffer. All buffers are made up of sterile pyrogen deionized distilled water and sterile filtered just prior to use. The second half of the sample is then spun, applied to the column and eluted in the same manner as the first half. The pH 7 protein peaks from both runs are pooled and treated further and the stacks are dismantled and repacked using new resins.

ii. High G force basket centrifuge QAE chromotography

A variable speed basket centrifuge equipped with a one hundred l. capacity is lined with a one micron polypropylene liner and loaded with about 3950 g of QAE-50 Sephadex. The liner, rotor, tubing, and all parts are sterilized either by autoclaving or soaking in 70% ethanol prior to use. The Sephadex is pre-swelled and sterilized in pH 7.0 ± 0.05 and 0.1 ionic strength imidazole-acetate buffer containing 25% ethanol. After the Sephadex bed has been packed for about five minutes at 220 X G (1140 RPM), the speed of the motor is reduced to 52 X G (550 RPM) and run another five minutes. Imidazole-acetate buffer without ethanol is applied to the bed through a Flood Jet ⅜ KSS 35 at 7 pounds pressure or ¼ K15 stainless steel nozzle at about 7.5 l/min throughout the packing procedure. After the bed is equilibrated with the buffer, 50 l of sample are applied and recycled twice (8 to 10 minutes each — total 20 minutes). Then imidazole-acetate buffer is flushed through the gel and added to the sample. The Sephadex is reclaimed by applying ph 4.0 and 0.1 ionic strength sodium-acetate to the bed to remove waste proteins. The bed is reequilibrated as above, and the next 50 l of sample may be applied as above. The protein from both runs is pooled, mixed, and a sample removed for biuret protein concentration determination. It is then diafiltrated against glycine saline buffer (pH = 6.80 ± 0.05 and conductivity = 13 mS) until the pH = 6.80 ± 0.05 and the conductivity = 12 - 15 mS. Samples of the pool and filtrates are collected for biuret protein concentration determination. Total time is less than one hour.

E. High speed spin

The pool is now high-speed spun in a Beckman J-21B centrifuge with a JCF-2 flow through rotor at 32,800 X G and 4° C at a flow rate of 350 ml/min. The rotor is sterilized with 70% ethanol and rinsed with non-pyrogenic $H_2O$ prior to use. A sample is removed for biuret protein concentration determination.

F. Sterile filtration

Immediately following the high-speed spin, the pool is prefiltered in preparation for bottling through a 0.20 micron Pall Ultipor DFA 3001 ARP filter (a non-asbestos, non-glass fiber containing filter) which has been autoclaved at 132° C for one hour. It is then final filtered through another sterile .20 micron Pall filter and then through a Millipore 0.45 micron HAWP 14250 membrane filter which has been autoclaved at 121 degrees for 20 minutes. Sterile technique is carefully followed during all stages of this operation. The 0.45 micron membrane filter is sterilely transferred to and cultured in 1000 ml of TSB culture media for 7 days. A sample of this culture is assayed for sterility on day 7.

4. Bottling, storage, and packaging

The intravenous immune serum globulin (human) is sterile filled into 40 ml vials which have been previously washed in non-pyrogenic distilled water and steam autoclaved for sterility. Sterilization of the immune serum globulin (human) is obtained either by Millipore filtration using a sterilized .45 micron prefilter and a 0.22 micron final filter or by a Pall filter system starting with a .45 micron prefilter and a 0.22 micron final filter. The filtered intravenous immune serum globulin (human) is collected and automatically pipetted into 40 ml bottles. These are sterilely capped and sealed. The bottled material is labeled, and stored for 2 weeks at either −20° C or 3 to 5° C until all tests have been completed. If all tests are passed, it is approved for administration.

The multiple injection 40 ml vials are individually labeled with proper label, lot number, and expiration date according to Section 73.50 Public Health Service regulations. They are placed in stainless steel locked boxed for refrigeration at −20° C or 3° to 5° C. When removed for distribution, the labeled vial is individually packed in a labeled box with lot number, expiration date, and Information Leaflet according to Section 73.52 Public Health Service regulations.

The IgG product is fully capable of intravenous administration without adverse reaction or effect. The advantages to be gained by the use of an intravenous human IgG that has not been denatured by preparation, or altered by chemical or enzymatic processes include the following: 1) prolonged half-life in the circulation, 2) higher maximal levels following intravenous administration, 3) maximal therapeutic activity, 4) no systemic reactions, and 5) painless route of administration allowing for 10 to 50 fold increase in dosage compared with other routes. Intravenous human IgG prepared by the described methods has been tested clinically in doses ranging from 20 mg/kg/day for ten days to 200 mg/kg/day for six days. The purpose in using the higher dose range was to achieve complete replacement of the total body IgG pool. In clinical trials, this high dose treatment schedule resulted in 11 of 13 patients with CMV interstitial-pneummonitus making complete recoveries. This is noteworthy, since past experience with this disease indicated that it was uniformly fatal. The total experience is with over 500 intravenous injections of this preparation with no undesirable side effects or reactions. Studies are proposed to use hyper-immune intravenous IgG, for not only prophylaxis but therapy of a number of viral and bacterial life threatening infections.

Albumin is isolated in significantly greater yields and purity than with the alcohol method. The described process makes possible a superior product at markedly reduced costs.

In summary, a new methodology has been developed for human plasma fractionation. The methods and technology can be characterized by 1) their simplicity, 2) the speed that each step can be performed, 3) the lack of rigid temperature requirements, since most of the processes can be carried out at room temperature, 4) the ease in scaling up to large industrial-scale volumes, 5) the removal of pyrogens and hepatitis associated antigen from plasma (at two stages or steps in the procedure), and 7) the isolation of undenatured natural material of highest purity and in significantly greater yields than can be accomplished with the current industrial-scale alcohol procedures.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of isolating and purifying natural immune gamma globulin for intravenous use and albumin from blood plasma, which method comprises:
   (A) intimately admixing a human blood plasma product containing gamma globulin and albumin and contaminating blood proteins, lipids, lipoproteins and proteolytic enzymes with finely divided sterile fumed silica,
   (B) separating the silica with adsorbed contaminating blood proteins, lipids and lipoproteins from the remaining stabilized plasma product,
   (C) adjusting the pH of the stabilized plasma product to about pH 6.8 to 7.2 and the conductivity to about 5 to 7 (at 22° C),
   (D) applying the stabilized plasma product to a strongly basic anion exchanger and separating purified gamma globulin therefrom,
   (E) eluting the albumin from the anion exchanger by applying a buffer of about pH 4.7 to 4.9 thereto, and
   (F) applying the eluted albumin to a strongly acid cation exchanger and separating purified albumin therefrom.

2. A method according to claim 1 wherein the separated gamma globulin is recycled to the anion exchanger at least once.

3. A method according to claim 1 wherein a buffer of about pH 5.7 to 5.9 is applied to the anion exchanger after separation of gamma globulin and before elution of albumin, and discarded.

4. A method according to claim 1 wherein said gamma globulin is further purified by diafiltration and sterile filtration.

5. A method according to claim 1 wherein said albumin is further purified by diafiltration and sterile filtration.

6. A method according to claim 1 wherein said ion exchanger treatments are carried out in a basket centrifuge under high gravity force chromatography.

7. A method according to claim 1 wherein:
   (A) said stabilized plasma product is applied to a strongly basic anion exchanger in a basket centrifuge, separated, recycled at least once and reseparated,
   (B) a buffer of about pH 5.7 to 5.9 is applied to the anion exchanger and discarded.
   (C) said eluted albumin is applied to a strongly acid cation exchanger in a basket centrifuge and separated, and
   (D) said gamma globulin and albumin are further and separately purified by diafiltration and sterile filtration.

8. A method of isolating and purifying immune gamma globulin for intravenous use and albumin from a silica stabilized blood plasma product containing gamma globulin and albumin, which method comprises:
   (A) adjusting the pH of the stabilized plasma product to about pH 6.8 to 7.2 and the conductivity to about 5 to 7 (at 22° C),
   (B) applying the stabilized plasma product to a strongly basic anion exchanger and separating purified gamma globulin therefrom,
   (C) eluting the albumin from the anion exchanger by applying a buffer of about pH 4.7 to 4.9 thereto, and
   (D) applying the eluted albumin to a strongly acid cation exchanger and separating purified albumin therefrom.

9. A method according to claim 8 wherein the separated gamma globulin is recycled to the anion exchanger at least once.

10. A method according to claim 8 wherein a buffer of about pH 5.7 to 5.9 is applied to the anion exchanger after separation of gamma globulin and before elution of albumin, and discarded.

11. A method according to claim 8 wherein said gamma globulin is further purified by diafiltration and sterile filtration.

12. A method according to claim 8 wherein said albumin is further purified by diafiltration and sterile filtration.

13. A method according to claim 8 wherein said ion exchange treatments are carried out in a basket centrifuge under high gravity force chromatography.

14. A method according to claim 8 wherein:
   (A) said stabilized plasma product is applied to a strongly basic anion exchanger in a basket centrifuge, separated, recycled at least once and reseparated,
   (B) a buffer of about pH 5.7 to 5.9 is applied to the anion exchanger and discarded,
   (C) said eluted albumin is applied to a strongly acid cation exchanger in a basket centrifuge and separated, and
   (D) said gamma globulin and albumin are further and separately purified by diafiltration and sterile filtration.

15. A method according to claim 1 wherein said blood plasma product is admixed with finely divided sterile fumed silica in wet form.

* * * * *

UNITED STATES PATENT AND TRADEMARK OFFICE
CERTIFICATE OF CORRECTION

PATENT NO. : 4,136,094
DATED : January 23, 1979
INVENTOR(S) : Richard M. Condie

It is certified that error appears in the above-identified patent and that said Letters Patent are hereby corrected as shown below:

On the title page, under "References Cited", "3,869,436 3/1976" should be --3,869,436  3/1975--.

Column 7, line 5, " $\frac{2}{3}$ " should be --1/8--.

Column 7, line 31, "=4.9" should be --$\simeq$ 4.9--.

Column 7, line 61, after "8.", insert --Bottle--.

Column 9, line 5, at the beginning of the line, omit "S".

Column 9, line 15, at the beginning of the line, omit "S".

Signed and Sealed this

Twenty-fourth Day of April 1979

[SEAL]

Attest:

RUTH C. MASON
Attesting Officer

DONALD W. BANNER
Commissioner of Patents and Trademarks